United States Patent [19]

Doner et al.

[11] Patent Number: 4,834,893

[45] Date of Patent: May 30, 1989

[54] SUBSTITUTED PHOSPHORODITHIOATES AND THEIR METAL SALTS AS MULTIFUNCTIONAL ADDITIVES

[75] Inventors: John P. Doner, Sewell; Liehpao O. Farng, Lawrenceville; Andrew G. Horodysky, Cherry Hill, all of N.J.

[73] Assignee: Mobil Oil Corporation, New York, N.Y.

[21] Appl. No.: 140,174

[22] Filed: Dec. 31, 1987

[51] Int. Cl.$^4$ ............................................ C10M 137/04
[52] U.S. Cl. .............................. 252/32.7 E; 252/46.6; 252/389.2; 252/400.2
[58] Field of Search .............. 252/32.7 E, 46.6, 389.2, 252/400.2

[56] References Cited

U.S. PATENT DOCUMENTS

| 3,235,497 | 2/1966 | Lee ................................ | 252/32.7 E |
| 3,324,032 | 6/1967 | O'Halloran et al. ........... | 252/32.7 E |
| 3,489,682 | 1/1970 | LeSuer ........................... | 252/32.7 E |
| 3,844,960 | 10/1974 | Breitigam et al. ............. | 252/32.7 E |

*Primary Examiner*—Jacqueline V. Howard
*Attorney, Agent, or Firm*—Alexander J. McKillop; Charles J. Speciale; Howard M. Flournoy

[57] ABSTRACT

Phosphorodithioate substituted carboxylic anhydride or acid derivates and their corresponding metal salts have been found to be effective multifunctional additives for various lubricants and fuels.

30 Claims, No Drawings

SUBSTITUTED PHOSPHORODITHIOATES AND THEIR METAL SALTS AS MULTIFUNCTIONAL ADDITIVES

BACKGROUND OF THE INVENTION

This invention relates to compositions of matter comprising phosphorodithioate derived succinic anhydride derivatives and their corresponding metal salts and to lubricant and liquid fuel compositions containing small additive amounts thereof.

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried, however, many of them are only marginally effective except at high concentrations. Improved antioxidants are clearly needed.

Antioxidants or oxidation inhibitors are used to minimize the effects of oil deterioration that occur when hot oil is contacted with air. The degree and rate of oxidation will depend on temperature, air and oil flow rates and, of particular importance, on the presence of metals that may catalytically promote oxidation. Antioxidants generally function by prevention of chain peroxide reaction and/or metal catalyst deactivation. They prevent the formation of acid sludges, darkening of the oil and increases in viscosity due to the formation of polymeric materials.

Water (moisture) is another critical problem. In spite of even extraordinary precautionary efforts water is found as a film or in minute droplets in vessels containing various hydrocarbon distillates. This brings about ideal conditions for corrosion and damage of metal surfaces of the vessels and the materials contained therein. Also in the lubrication of internal combustion engines, for example, quantities of water are often present as a separate phase within the lubricating system. Another serious problem in respect to metallic surfaces in contact with adjacent metallic surfaces is the surface wear caused by the contact of such surfaces. One material capable of simultaneously effectively coping with such problems as these is highly desireous.

It has now been found that the use of phosphorodithioate derived succinic anhydride derivatives and their corresponding metal salts provide exceptional antioxidant and antiwear activity with significant rust inhibiting, and potential corrosion inhibiting properties. These remarkable benefits are to be expected for a variety of synthetic and mineral oil based lubricants and liquid hydrocarbon fuels.

To the best of our knowledge, these compositions have not been previously used as multifunctional additives in lubricating oils, greases, or fuel applications. The additive products themselves and lubricant compositions thereof are both believed to be novel.

The use of phophorodithioate compositions, especially the corresponding salts of phosphorodithioate, such as Zinc dialkylphosphorodithioates (commonly known as zinc dithiophosphates) have found widespread commerical use for several decades in engine oils as multifunctional antiwear, peroxide decomposing, and bearing corrosion inhibiting additives.

The use of succinic anhydride derivatives has been extensively reported as having beneficial antirust properties as well as detergency/dispersancy characteristics. It is an object of this invention to provide lubricant and fuel compositions of improved multifunctional capability having, e.g. antioxidant, antiwear and antirust/corrosion characteristics. It is a further object to provide novel additive products derived form phosphorodithioate substituted carboxylic acid anhydride derivatives and their corresponding metal salts.

SUMMARY OF THE INVENTION

This application is directed to compositions containing small additive concentrations of phosphorodithioate derived alkenyl carboxylic acid or anhydride derivatives, such as (O,O-di-2-ethylhexyl-S-2-hydroxypropyl) phosphorodithioate substituted dodecenyl succinic acid ester; and the metal salts of phosphorodithioate derived alkenyl carboxylic anhydride derivatives, such as the lithium and copper salts of the reaction product O,O-di-2-ethylhexyl-S-2-hydroxypropyl phosphorodithioate with polyisobutenyl or dodecenyl succinic anhydride possess excellent antioxidant properties coupled with very good antiwear and antirust activities.

Although applicants do not wish to be held to a particular theory, both the phosphorodithioate alcohol moiety and the metallic moiety are believed to provide the basis for the synergistic antioxidant activity and each of which are believed subsequently enhanced by the succinic anhydride coupling moiety. The phosphorodithioate group is believed to contribute additional antiwear properties to these novel additives. The carboxylic anhydride moieties may additionally contribute significant antirust and/or anticorrosion properties to this new class of additives. All of these beneficial properties are believed to be enhanced as a result of internal synergism.

This unique internal synergism concept is believed to be applicable to similar structures containing (a) metal carboxylated groups, (b) phosphorodithioate derived alcohol groups, and (c) succinic acid/ester linkages, or phthalic acid/ester linkages, or related dibasic acid, diester groups within the same molecule.

DESCRIPTION OF PREFERRED EMBODIMENTS

O,O-Dialkyl phosphorodithioic acids made by the reaction of alcohols with phosphorus pentasulfide or O,O-diaryl phosphorodithioic acids made by the reaction of phenols with phosphorus pentasulfide were reacted with alkylene oxides to form phosphorodithioate-derived alcohols. However, any suitable method of preparation may be used.

These alcohols were then reacted (generally in stoichometric amounts) with carboxylic anhydrides (substituted succinic or phthalic anhydrides) to form dibasic acid esters, or diesters, as generally described below:

Equation 1

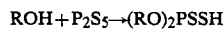

Where R is $C_3$ to about $C_{30}$ hydrocarbyl or $C_3$ to about $C_{30}$ hydrocarbyloxyhydrocarbylene or mixtures thereof. Unless otherwise specified hydrocarbyl as used here and herein below includes alkyl, alkenyl, cycloalkyl, aryl, aralkyl or alkaryl groups which may have substituted thereon other groups, e.g., alkoxy or alkylthio groups, etc.

Equation 2

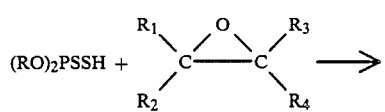

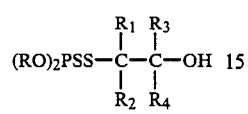

where $R_1$, $R_2$, $R_3$ and $R_4$ are hydrogens or are individually selected from $C_1$ to about $C_{30}$ hydrocarbyl and R is as defined hereinabove.

Equation 3

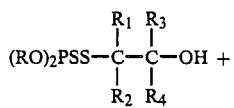

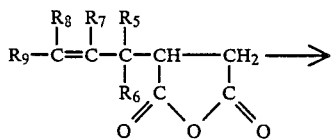

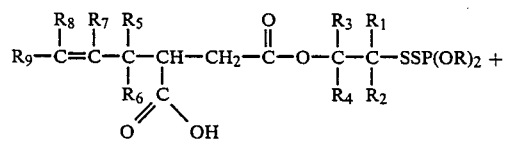

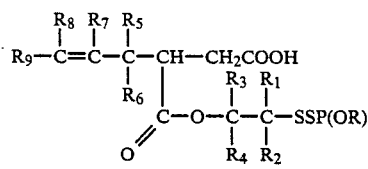

Where $R_5$ to $R_9$ are as defined herein below.

These substituted succinic acid-ester derivatives were subsequently converted to their corresponding metal salts by reaction with almost molar quantities, or less than molar quantities, or more than molar quantities of metal ions to make neutral, acidic, or basic salts (Equation 4). Generally, the metal ions used in this invention can be alkaline, alkali earth, or transition metals or any other suitable metal; and the metallic compounds used in the reactions can be organometallic compounds, or inorganic metal salts.

Equation 4

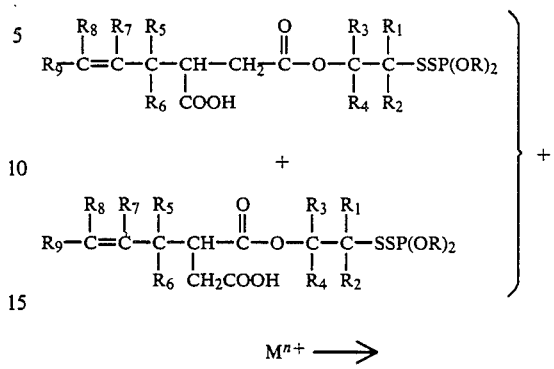

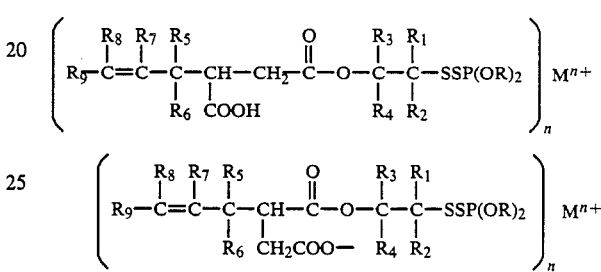

Where $R_5$ to $R_8$ are hydrogen or hydrocarbyl groups or aralkyl groups or cycloalkyl groups of $C_1$–$C_{10}$ and $R_9$ is a hydrocarbon based group of $C_1$ to about $C_{60}$ and wherein n is 1–3.

Generally speaking the various reaction times, temperatures, pressures and quantities of reactive materials may vary widely and are not critical.

The additives may be incorporated into any suitable lubricating media which comprises oils of lubricating viscosity, e.g., mineral or synthetic; or mixtures of mineral and synthetic or greases in which the aforementioned oils are employed as a vehicle or into such functional fluids as hydraulic fluids, brake fluids, power transmission fluids and the like. In general, mineral oils and/or synthetic, employed as the lubricant oil, or grease vehicle may be of any suitable lubricating viscosity range, as for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation.

In instances where synthetic oil, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

Fully formulated lubricating oils may include a variety of additives (for their known purpose) such as dispersants, detergents, inhibitors, antiwear agents, antioxidant, antifoam, pour depressant and other additives including phenates, sulfonates and zinc dithiophosphates. As hereinbefore indicated, the aforementioned additive compounds may be incorporated as multifunctional agents in grease compositions. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above described additives, are combined with a grease forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickners may be employed which do not melt and dissolve when used at the required temperature within a particular environment; soap thickeners such as metallic (lithium or calcium) soaps including hydroxy stearate and/or stearate soaps can be used however, in all other respects, any material which is normally employed for thickening or gelling hydrocarbon fluids or forming greases can be used in preparing the aforementioned improved greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid.

The entire amount of thickener need not be derived from the aforementioned preferred members significant benefit can be attached using as little thereof as about 15% by weight of the total thickener. A complementary amount, i.e., up to about 85% by weight of wide variety of thickening agents can be used in the grease of this invention. Included among the other useful thickening agents are alkali and alkaline earth metal soaps of methyl-12-hydroxystearate, diesters of a $C_4$ to $C_{12}$ dicarboxylic acid and tall oil fatty acids. Other alkali or alkaline earth metal fatty acids containing from 12 to 30 carbon atoms and no free hydroxyl may be used. These include soaps of stearic and oleic acids.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and and soaps of low-, intermediate- and high-molecular weight acids and of nut oil acids.

As has been disclosed hereinabove, the reaction products are useful as multifunctional antiwear/antioxidant/antirust agents. They are added to the lubricating medium in amounts sufficient to impart such properties to the lubricant. More particularly, such properties will be imparted to the lubricant by adding from about 0.01% to about 10% by weight, preferably from about 0.01% to about 3%, of the neat product.

The following examples are exemplary only and are not intended as limitations.

EXAMPLE 1

Propoxylated Di-(2-ethylhexyl) Phosphorodithioic Acid (O,O-di-2-ethylhexyl-S-(2-hydroxypropyl) phosphorodithioate)

Approximately 708.6 grams of di-(2-ethylhexyl) phosphorodithioic acid (commercially obtained) was charged into a 1-l stirred reactor equipped with a condensor and a thermometer. Approximately 116.2 grams of propylene oxide (equal molar) was slowly added over a course of 2 hours. The reaction temperature was controlled at or below 40° C. by using ice-water bath for cooling. At the end of the addition, the reaction mixture changed its color from dark-greenish to light yellowish. It weighed approximately 825 grams.

EXAMPLE 2

[(O,O-di-2-Ethylhexyl-S-(2-hydroxypropyl) phosphorodithioate) substituted dodecenyl succinic acid ester]

Approximately 412.5 grams of the above product of Example 1, and 266.0 grams (1.0 mole) of dodecenyl succinic anhydride were mixed together in a 1-l, 4-neck reactor equipped with thermometer, condenser, agitator and nitrogen sparger. This mixture was heated at 82°±2° C. over a course of 6 hours and at the end of the reaction, the desired product was obtained as a yellow, viscous liquid.

EXAMPLE 3

Lithium salt of O,O-di-(2-ethylhexyl)-S-(2-hydroxypropyl) phosphorodithioate substituted dodecenyl succinic acid ester Approximately 167 grams of the above product of Example 2 (0.25 mol), 10.5 grams of lithium hydroxide monohydrate (LiOH $H_2O$, 0.25 mol), and 150 millimeters of toluene were charged to a reaction vessel. This mixture was heated up and refluxed at 115°±5° C. over a course of 5 hours. A total amount of 7.7 millimeters of water was collected in a Dean Stark trap. At the end of the reaction, the solvents (residual water and toluene) were removed by vacuum distillation, and the product was filtered through diatomaceous earth to remove unreacted solids. This product was a yellow, viscous fluid and contains 0.98% of lithium (theory, 1.02%), and 4.36% phosphorus (theory, 4.53%).

EXAMPLE 4

Cupric salt of O,O-di(2-ethylhexyl)-S-(2-hydroxypropyl) phosphorodithioate substituted dodecenyl succinic acid ester Approximately 334 grams of the above product of Example 2 (0.5 mol), 27.6 grams of basic copper (II) carbonate $(Cu(OH)_2CuCO_3, 0.125$ mol), an 300 millimeters of toluene were mixed into a reactor. This mixture was refluxed at 114°±2° C. over a course of 7 hours with agitation and under nitrogen blanket. 2.7 Millimeters of water were collected in the Dean Stark trap. Approximately 200 grams diluent oil (100 second solvent paraffinic neutral lubricating oil) was added to reduce viscosity and improve handling. The residual solvent was removed by vacuum distillation at 125°±2° C., and the product was filtered off some insoluble solids. This gave 556 grams of dark liquid containing 2.66% of phosphorus (theory, 2.79%) and 2.1% of copper (theory, 2.85%).

Aliquots of the products of examples 2 and 3 were embedded into fully formulated oils, and base greases, and evaluated for antioxidant performance (Table 6), antiwear activity (Table 4), copper strip corrosivity (Table 7), and rust prevention (Table 5) characteristics as shown below. Aliquots of the product of Example 4 were blended into fully formulated oils and evaluated by Catalytic Oxidation Test at 325° F. for 40 hours (Table 1); Catalytic Oxidation Test at 260° F. for 80 hours (Table 2); and Catalytic Oxidation Test at 375° F. for 24 hours (Table 3). It is also noted that the novel additives in accordance with this invention may be used to advantage in conjunction with any known lubricant additive system without deleterious effect.

CATALYTIC OXIDATION TEST

The test lubricant composition is subjected to a stream of air which is bubbled through the composition at a rate of 5 liters per hour at the specified temperature for the required number of hours. Present in the composition (comprising a 150 second solvent refined paraffinic bright oil) in addition to the additive compound were metals commonly used as materials to construct engines namely:

(a) 15.6 square inch of sand-blasted iron wire;
(b) 0.78 square inch of polished copper wire;
(c) 0.87 square inch of polished aluminum wire; and
(d) 0.107 square inch of polished lead surface.

The test results are reported below in tables 1, 2, and 3.

TABLE 1

Catalytic Oxidation Test-40 Hours at 325° F.

| | Additive conc. (wt %) | Change in Acid Value | % Change in Viscosity | Sludge Rating |
|---|---|---|---|---|
| Base Oil (150 second, fully formulated, solvent refined paraffinic bright oil containing deformant/demulsifier/antiwear/anticorrosion/EP/antirust performance package) | — | 2.58 | 30.61 | Nil |
| Example 4 | 0.5 | 1.81 | 27.15 | Trace |

TABLE 2

Catalytic Oxidation Test-80 Hours at 260° F.

| | Additive conc. (wt %) | Change in Acid Value | % Change in Viscosity | Sludge Rating |
|---|---|---|---|---|
| Base Oil (fully formulated mineral oil as described in Table 1) | — | 0.01 | 6.49 | Nil |
| Example 4 | 0.5 | 0.03 | 4.95 | Nil |

TABLE 3

Catalytic Oxidation Test-24 Hours at 375° F.

| | Additive conc. (wt %) | Change in Acid Value | % Change in Viscosity | Sludge Rating |
|---|---|---|---|---|
| Base Oil (fully formulated mineral oil as described in Table 1) | — | 6.53 | 177.9 | Medium |
| Example 4 | 0.5 | 3.62 | 103.1 | Light |

Small concentrations of the product of Example 4 controls the increase in viscosity, and the increase in acid number of a fully formulated mineral oil based gear oil extremely well and over a wide range of testing temperature as shown in Tables 1, 2, and 3.

Small quantities of the products of Examples 2 and 3 were blended into greases and evaluated for antiwear performance using the Four-Ball Wear Test (ASTM D2266, Table 4); antirust performance (ASTM D1743 for distilled water and ASTM D1743 for 3% sea water, Table 5); oxidation stability using the Bomb Oxidation Test (Method D942, Table 6); and copper strip corrosivity using the Corrosivity Test (ASTM D4048, Table 7).

A small concentration of the product of Example 4, blended into a synthetic lithium grease was also tested for its antiwear properties according to the Four-Ball Wear Test. The results are set forth in Table 4. The products of the examples and comparative examples were tested in the 4-ball test using a modified 4-ball machine. In this test, three stationary balls are placed in a lubricant cup and a lubricant containing the additive to be tested is added thereto. A fourth ball is place on a chuck mounted on a device which can be used to spin the ball at known speeds and loads. Various percentages by weight of each product was placed in the blend. The samples were tested at 75° C. at a load of 40 kilograms and 1200 rpm for 60 minutes.

Samples of the lithium base grease were also tested as indicated above in the well known test procedures as identified.

TABLE 4

Four Ball Wear Test
ASTM D2266 (1200 rpm, 75° C., 40 kg load, 60 minutes)

| Example No. | Additive Conc. (wt %) | Wear Scar Diameter (mm) |
|---|---|---|
| Base grease (ISO 220 synthetic oil lithium complex thickened, additive free grease) | — | 0.6 |
| Example 2 | 2.5 | 0.4 |
| Example 3 | 2.5 | 0.4 |

TABLE 5

Rust Test
ASTM D1743: Distilled Water; D1743: 3% Sea Water

| Example No. | Additive Conc. (wt %) | Rust Rating Distilled Water | Rust Rating 3% Sea Water |
|---|---|---|---|
| Base grease (ISO 220 synthetic oil lithium complex thickened grease) | — | 3,3 | 3,3 |
| Example 2 | 2.5 | — | 1,3 |
| Example 3 | 1.0 | 1,3 | — |
|  | 2.5 | — | 1,3 |

Rust test rating
1 = no rusting
2 = no more than 3 small spots no greater than 1 mm
3 = rusting greater than rating 2

TABLE 6

ASTM D942 Bomb Oxidation Test (100° C.)

| Example No. | Additive Conc. (wt %) | psi Loss 100 hr. | psi Loss 500 hr. |
|---|---|---|---|
| Base grease (ISO 220 synthetic oil lithium complex thickened grease) | — | 1 | * |
| Example 2 | 2.5 | 1 | 4 |
| Example 3 | 2.5 | 0 | 1 |

*The test stopped at 286 hr. with 92 psig loss.

TABLE 7

ASTM D4048 Copper Strip Corrosivity Test (100° C., 24 hours)

| Example No. | Additive Conc. (wt %) | Corrosivity Rating |
|---|---|---|
| Base grease (ISO VG 220 synthetic oil lithium complex thickened grease) | — | 1b |
| Example 2 | 2.5 | 1b |
| Example 3 | 2.5 | 1b |

As can be seen from the above test results, the products described exhibit considerable antiwear activity, rust prevention properties, and antioxidation characteristics, while showing no deleterious effect or corrosivity to the base lubricant.

The use of additive concentrations of phosphorodithioate derived carboxylic anhydride derivatives and their corresponding metal salts in premium quality automotive and industrial lubricants will significantly enhance stability, extend service life, reduce wear, and prevent or inhibit the rust of the metal surfaces. These novel compositions and additive products described are useful at low concentrations and do not contain any potentially undesirable chlorides.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A composition comprising a major amount of an oil of lubricating viscosity or grease or other solid lubricant prepared therefrom and a minor multifunctional antioxidant/antirust/antiwear/corrosion inhibiting amount of a phosphorodithioate derived alkenyl carboxylic anhydride or acid derivative thereof or their corresponding metal salts or mixtures thereof wherein said phosphorodithioate derived alkenyl carboxylic anhydride is a product of reaction made by
   (a) the reaction of a phosphorodithioic acid is substantially equimolar amount with an . . . alkylene oxide to form phosphorodithioic-derived alcohols which are then;
   (b) reacted in substantially stoichiometric amount with carboxylic dibasic anhydrides or acids to form the corresponding dibasic acid esters or diesters.

2. The composition of claim 1 wherein said phosphorodithioate derived alkenyl carboxylic anhydride is a product of reaction made by
   (a) the reaction of a phosphorodithioic acid with a $C_2$ to about a $C_{122}$ alkylene oxide thereby forming phosphorodithioate-derived alcohols which are then;
   (b) reacted with about $C_8$ to about a $C_{100}$ carboxylic dibasic anhydride or acid thereby forming the corresponding dibasic acid esters or diesters.

3. The composition of claim 1 wherein said products are converted to their corresponding metal salt by reaction with almost molar quantities, or less than molar quantities, or more than molar quantities of metal ions.

4. The composition of claim 2 wherein said products are converted to their corresponding metal salt by reaction with almost molar quantities, or less than molar quantities, or more than molar quatities of metal ions.

5. The composition of claim 1 wherein the said metal is selected from the group consisting of alkali, alkaline earth and transition metals.

6. The composition of claim 5 wherein the said metal is lithium.

7. The composition of claim 5 wherein the said metal is copper.

8. The composition of claim 1 wherein the said multifunctional derivative is O,O-(di-2-ethylhexyl)-S-(2-hydroxypropyl) phosphorodithioate substituted dodecenyl succinic acid ester.

9. The composition of claim 1 wherein the said multifunctional derivative is the lithium salt of O,O-di-2-ethylhexyl)-S-(2-hydroxypropyl) phosphorodithioate substituted dodecenyl succinic acid esters.

10. The composition of claim 1 wherein the said multifunctional derivative is the cupric salt of O,O-di(2-ethylhexyl)-S-(2-hydroxypropyl) phosphorodithioate substituted dodecenyl succinic and esters.

11. The composition of claim 1 wherein said oil of lubricating viscosity is selected from mineral oils, synthetic oils and mixtures thereof.

12. The composition of claim 11 wherein said oil is a mineral oil.

13. The composition of claim 11 wherein said oil is a synthetic oil.

14. The composition of claim 10 wherein said oil is a mixture of synthetic and mineral oils.

15. The composition of claim 1 wherein said composition is a grease composition.

16. The composition of claim 15 wherein said grease is synthetic and/or mineral oil lithium complex thickened grease.

17. A product of reaction made by reacting a phosphorodithioate acid in substantially equimolar amounts with an alkylene oxide to form a phosphorodithioate derived alcohol which is then reacted in substantially stoichiometric amounts with a dibasic carboxylic acid or anhydride to form multifunctional lubricant additive products comprising phosphorodithioic acid derived dibasic acid esters or diesters.

18. The product of claim 17 wherein the phosphorodithioic acid is a dialkyl or a diaryl phosphorodithioic acid.

19. The product of claim 7 wherein said acid is di-(2-ethylhexyl)-phosphorodithioic acid.

20. The product of claim 17 wherein the additive product is 0,O-(di-2-ethylhexyl)-S-(2-hydroxypropyl) phosphorothioate substituted dodecenyl succinic acid ester).

21. The product of claim 18 wherein said product is converted to a corresponding metal salt by reaction with almost molar quantities, or less than molar quantities, or more than molar quantities of metal ions.

22. The product of claim 21 wherein said metal is selected from the groups consisting of alkali, alkaline earth and transition metals.

23. The product of claim 22 herein said metal is lithium.

24. The product of claim 23 wherein said metal is copper.

25. The product of claim 23 wherein the additive product is the lithium salt of O,O-di(2-ethylhexyl)-S-(2-hydroxypropyl) phosphorodithioate substituted dodecenyl succinic and esters.

26. The product of claim 24 wherein the said metal is the cupric salt of O,O-di(2-ethylhexyl)-S-(2-hydroxypropyl) phosphorodithioate substituted dodecenyl succinic and esters.

27. The additive product of claim 17 comprising at least one or more of the following general structures or mixtures thereof:

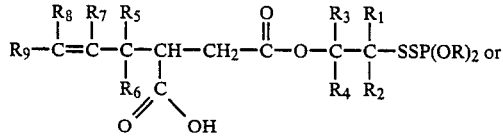

-continued

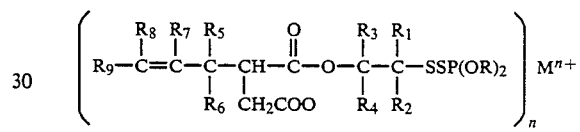

wherein R is $C_3$ to about $C_{30}$ hydrocarbyl or hydrocarbyl-oxyhydrocarbylene or mixtures thereof; $R_1$, $R_2$, $R_3$ and $R_4$ are hydrogens or are individually selected from $C_1$ to about $C_{30}$ hydrocarbyl and $R_5$ to $R_8$ are hydrogens or hydrocarbyl groups or aralkyl or cycloalkyl groups having from 1 to about 10 carbon atoms and where $R_9$ is a $C_1$ to about a $C_{60}$ hydrocarbon based group.

28. The additive product of claim 22 comprising at least one or more of the following general structures:

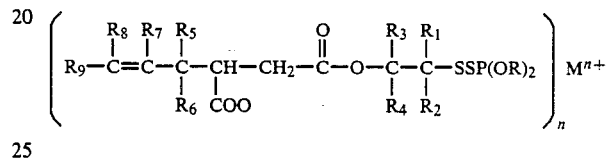

or

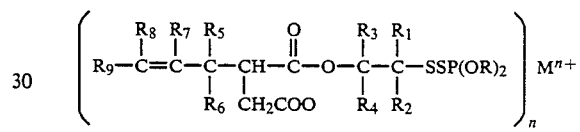

wherein n is 1-3 and R is $C_3$ to about $C_{30}$ hydrocarbyl or hydrocarbyl-oxyhydrocarbylene or mixtures thereor; $R_1$ $R_2$ $R_3$ and $R_4$ are hydrogens or are individually selected from $C_1$ to about $C_{30}$ hydrocarbyl and $R_5$ to $R_8$ are hydrogens or hydrocarbyl groups or aralkyl or cycloalkyl groups having from 1 to about 10 carbon atoms and where $R_9$ is a $C_1$ to about a $C_{60}$ hydrocarbon based group.

29. The additive product of claim 28 wherein the metal is lithium.

30. The additive product of claim 28 wherein the metal is copper.

* * * * *